United States Patent [19]

Yokokoji et al.

[11] Patent Number: 5,419,851
[45] Date of Patent: May 30, 1995

[54] DIFLUORO-DERIVATIVE COMPOUNDS AND LIQUID CRYSTAL COMPOSITIONS CONTAINING THEM

[75] Inventors: Osamu Yokokoji; Jun Irisawa; Hidemasa Koh, all of Yokohama, Japan

[73] Assignee: Asahi Glass Company Ltd., Tokyo, Japan

[21] Appl. No.: 211,625

[22] PCT Filed: Sep. 1, 1993

[86] PCT No.: PCT/JP93/01235
§ 371 Date: Apr. 20, 1994
§ 102(e) Date: Apr. 20, 1994

[87] PCT Pub. No.: WO94/05613
PCT Pub. Date: Mar. 17, 1994

[30] Foreign Application Priority Data

Sep. 4, 1992 [JP] Japan .................... 4-263027

[51] Int. Cl.$^6$ .............. C09K 19/30; C09K 19/52; C07C 25/13; G02F 1/13

[52] U.S. Cl. .............. 252/299.63; 252/299.01; 252/299.61; 252/299.64; 252/299.65; 252/299.66; 544/335; 549/380; 560/8; 570/127; 359/103

[58] Field of Search .......... 252/299.1, 299.64, 299.65, 252/299.66, 299.67; 544/335; 546/1; 549/13, 369, 380; 560/8; 570/127; 359/103

[56] References Cited

PUBLICATIONS

CA96: 1991852, Abstract, 1982.

*Primary Examiner*—Shean Wu
*Attorney, Agent, or Firm*—Oblon, Spivak, McClelland, Maier, & Neustadt

[57] ABSTRACT

The present invention provides a difluoro-derivative compound of the formula $R^1-(A^1-Y^1)_m-A^2-CF=CF-C\equiv C-A^3-(Y^2-A^4)_n-R^2$ (wherein each of $A^1$ to $A^4$ is a trans-1,4-cyclohexylene group, a 1,4-cyclohexenylene group or a 1,4-phenylene group, each of m and n is 0 or 1, and each of $R^1$ and $R^2$ is a $C_{1-10}$ alkyl group, a halogen atom or a cyano group).

The compound of the present invention has a low viscosity and is stable against lights, and a high speed response is expected by using it for a liquid crystal composition.

20 Claims, No Drawings

DIFLUORO-DERIVATIVE COMPOUNDS AND LIQUID CRYSTAL COMPOSITIONS CONTAINING THEM

TECHNICAL FIELD

The present invention relates to difluoro-derivative compounds, compounds having a liquid crystal property selected from such derivatives, liquid crystal compositions containing the difluoro-derivative compounds, and liquid crystal electro-optical devices using the liquid crystal compositions.

BACKGROUND ART

Liquid crystal display devices have been used for watches and electronic calculators and in recent years for various applications including measuring devices, automobile meters, copying machines, cameras, display devices for office appliances and display devices for consumer products. Accordingly, various functions including a wide temperature range for operation, a low voltage for driving, a high response speed, a high contrast ratio, a wide visual angle and chemical stability, are required for such liquid display devices.

However, at present, there is no single material which by itself satisfies all of such requirements, and it is common to satisfy such requirements by a liquid crystal composition prepared by mixing a plurality of liquid crystal materials and non-liquid crystal materials. Accordingly, it is desired to develop a liquid crystal material or a non-liquid crystal material which is excellent in one or more functions, if not in all the required functions.

In the field of the display device using liquid crystal, it is desired to improve its performance. For this purpose, low voltage driving, highly fine display, a high contrast ratio, a wide visual angle characteristic, a low temperature response characteristic and a wide range of driving temperature are, for example, desired. These functions have a tendency such that when some of them are improved, others have to be sacrificed.

Recently, improvement of a response speed is particularly desired. For example, in driving the device by an electrical cell, low voltage drive and high speed response are desired; in e.g. the office appliances, highly fine display and high speed response are required; and in the display for automobiles, low temperature response or high speed response within a wide temperature range for operation is desired.

In this respect, several methods for improvement are conceivable. One of them is to adopt a liquid crystal composition having a low viscosity. Namely, if the viscosity of the liquid crystal composition is reduced, the response speed can be improved so that a display will be possible at a practical speed even at a low temperature. Further, if the response speed may be at a level equal to the conventional speed, it will be possible to drive the device at a lower voltage, or a higher duty drive or highly fine drive, will be possible.

For such a purpose, a p,p'-disubstituted difluorostilbene compound has been proposed, as disclosed at the 16th Liquid Crystal Discussion Meeting. This compound has a chemical structure as shown by the following formula (3):

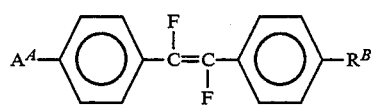

(3)

provided that in the formula (3), each of $R^A$ and $R^B$ is a n-alkyl group, a n-alkoxy group or a n-alkoxycarbonyl group.

The compound of this formula (3) has a low viscosity and has the stability against light improved over a stilbene compound which is not substituted by fluorine. However, as compared with commonly employed liquid crystal compounds, its stability against light is still poor, whereby in many cases, the useful environment has been rather limited, or it has been required to use an ultraviolet ray-preventive film.

Accordingly, a liquid crystal material having a low viscosity and having a high stability against light, has been desired.

It is an object of the present invention to provide a novel material thereby to solve the above problem.

The present invention provides a difluoro-derivative compound of the following formula (1):

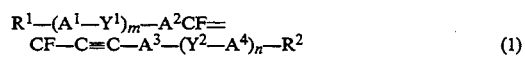

(1)

provided that in the formula (1), $A^1$, $A^2$, $A^3$, $A^4$, $Y^1$, $Y^2$, m, n, $R^1$ and $R^2$ are as follows:

each of $A^1$, $A^2$, $A^3$ and $A^4$, which are independent from one another, is a cyclic group selected from a trans-1,4-cyclohexylene group, a 1,4-cyclohexenylene group and a 1,4-phenylene group, wherein each of such cyclic groups is unsubstituted or substituted by one or more halogen atoms or cyano groups, one or more =CH— groups constituting rings of such cyclic groups may be substituted by nitrogen atoms, and one or more —CH$_2$— groups constituting rings of such cyclic groups may be substituted by oxygen atoms or sulfur atoms;

each of $Y^1$ and $Y^2$, which are independent from each other, is —COO—, —OCO—, —C≡C—, —CH$_2$CH$_2$—, —CH=CH—, —OCH$_2$—, —CH$_2$O— or a single bond;

each of m and n, which are independent from each other, is 0 or 1; and each of $R^1$ and $R^2$ which are independent from each other, is a C$_{1-10}$ alkyl group, a halogen atom or a cyano group, provided that in the case of the alkyl group, an oxygen atom, a carbonyloxy group or an oxycarbonyl group may be interposed in a carbon-carbon bond of the alkyl group or in a carbon-carbon bond between this alkyl group and the adjacent cyclic group, some of carbon-carbon bonds in the alkyl group may be triple bonds or double bonds, one —CH$_2$— group in the alkyl group may be substituted by a carbonyl group, and some or all of hydrogen atoms in the alkyl group may be substituted by fluorine atoms.

The present invention also provides a difluoro-derivative compound of the formula (2) $R^1$—A$^2$—CF=CF—C≡C—A$^3$—R$^2$ (wherein A$^2$, A$^3$, $R^1$ and $R^2$ are as defined with respect to the formula (1)), a compound having a liquid crystal property selected from such derivatives, and a liquid crystal composition containing a compound of the formula (1) or (2).

Further, the present invention provides a liquid crystal electro-optical device having a compound of the formula (1) or (2) interposed between substrates provided with electrodes.

The compound of the formula (1) of the present invention has a low viscosity, and it is excellent in compatibility with other liquid crystals or non-liquid crystals and is a material which is chemically stable particularly against light.

The following compounds may be mentioned to show the specific structures of the compound of the present invention. As a typical compound having two rings, the following compound may be mentioned.

$$R^1-A^2-CF=CF-C\equiv C-A^3-R^2 \qquad (4)$$

More specifically, the compound of the formula (4) includes the following compounds. In the following description, "—Ph—" represents a 1,4-phenylene group, "—Cy—" represents a trans-1,4-cyclohexylene group and "—Ch—" represents a 1,4-cyclohexenylene group. This applies not only to the compound of the formula (4) but also to other compounds. The cyclohexenylene group is preferably a 4-substituted 1-cyclohexenyl group.

$$R^1-Ph-CF=CF-C\equiv C-Ph-R^2 \qquad (4A)$$

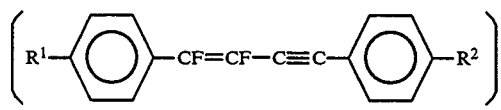

The following compound may be mentioned as a compound of the formula (4A) wherein the 1,4-phenylene groups are replaced by trans-1,4-cyclohexylene groups;

$$R^1-Cy-CF=CF-C\equiv C-Cy-R^2 \qquad (4B)$$

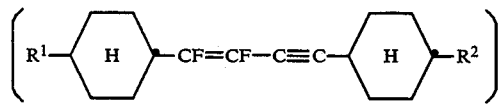

Further, the following compound may be mentioned as a compound of the formula (4A) wherein the 1,4-phenylene groups are replaced by 1,4-cyclohexylene groups;

$$R^1-Ch-CF=CF-C\equiv C-Ch-R^2 \qquad (4C)$$

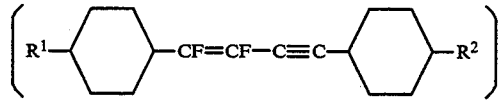

Further, the following compound may be mentioned as a compound of the formula (4A) wherein one of the 1,4-phenylene groups is replaced by a trans-1,4-cyclohexylene group;

$$R^1-Ph-CF=CF-C\equiv C-Cy-R^2 \qquad (4D)$$

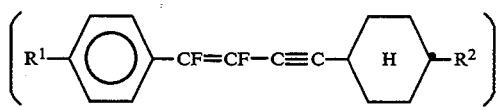

Further, the following compound may be mentioned as a compound of the formula (4A) wherein one of the 1,4phenylene groups is replaced by a 1,4-cyclohexenylene group;

$$R^1-Ph-CF=CF-C\equiv C-Ch-R^2 \qquad (4E)$$

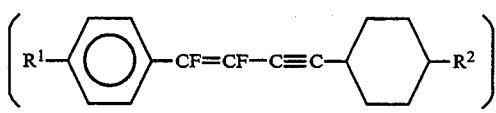

Further, the following compound may be mentioned as a compound of the formula (4A) wherein one of the 1,4-phenylene groups is replaced by a trans-1,4-cyclohexylene group and the other is replaced by a 1,4-cyclohexenylene group;

$$R^1-Cy-CF=CF-C\equiv C-Ch-R^2 \qquad (4F)$$

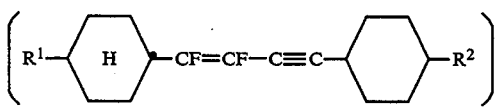

Further, the following compound may be mentioned as a compound of the formula (4A) wherein the 1,4-phenylene groups are phenylene groups with some of hydrogen atoms replaced by fluorine atoms. Here, "PhF" represents a monofluoro-1,4-phenylene group or a polyfluoro-1,4-phenylene group, provided that each of j and k which are independent from each other, is an integer of from 1 to 4.

$$R^1-PhF-CF=CF-C\equiv C-PhF-R^2 \qquad (4G)$$

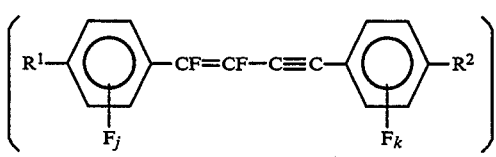

Further, the following compounds may be mentioned as compounds having three rings:

$$R^1-A^1-A^2-CF=CF-C\equiv C-A^3-R^2 \qquad (5)$$

$$R^1-A^2-CF=CF-C\equiv C-A^3-A^4-R^2 \qquad (6)$$

More specifically, the following compounds may be mentioned as the compound of the formula (5):

$$R^1-Ph-Ph-CF=CF-C\equiv C-Ph-R^2 \qquad (5A)$$

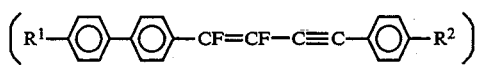

| | |
|---|---|
| $R^1$—Cy—Cy—CF=CF—C≡C—Cy—$R^2$ | (5B) |
| $R^1$—Ch—Ch—CF=CF—C≡C—Ch—$R^2$ | (5C) |
| $R^1$—Ph—Ph—CF=CF—C≡C—Cy—$R^2$ | (5D) |
| $R^1$—Ph—Ph—CF=CF—C≡C—Ch—$R^2$ | (5E) |
| $R^1$—Cy—Cy—CF=CF—C≡C—Ph—$R^3$ | (5F) |
| $R^1$—Cy—Cy—CF=CF—C≡C—Ch—$R^2$ | (5G) |
| $R^1$—Ch—Ch—CF=CF—C≡C—Ph—$R^2$ | (5H) |
| $R^1$—Ch—Ch—CF=CF—C≡C—Cy—$R^2$ | (5I) |
| $R^1$—Cy—Ph—CF=CF—C≡C—Ph—$R^2$ | (5J) |
| $R^1$—Ph—Cy—CF=CF—C≡C—Ph—$R^2$ | (5K) |
| $R^1$—Ph—Ch—CF=CF—C≡C—Ph—$R^2$ | (5L) |
| $R^1$—Ch—Ph—CF=CF—C≡C—Ph—$R^2$ | (5M) |
| $R^1$—Cy—Ch—CF=CF—C≡C—Ph—$R^2$ | (5N) |
| $R^1$—CH—Cy—CF=CF—C≡C—Ph—$R^2$ | (5O) |
| $R^1$—Ph—Cy—CF=CF—C≡C—Cy—$R^2$ | (5P) |
| $R^1$—Cy—Ph—CF=CF—C≡C—Cy—$R^2$ | (5Q) |
| $R^1$—Ph—Ch—CF=CF—C≡C—Cy—$R^2$ | (5R) |
| $R^1$—CH—Ph—CF=CF—C≡C—Cy—$R^2$ | (5S) |
| $R^1$—Cy—Ch—CF=CF—C≡C—Cy—$R^2$ | (5T) |
| $R^1$—Ch—Cy—CF=CF—C≡C—Cy—$R^2$ | (5U) |
| $R^1$—Ph—Cy—CF=CF—C≡C—Ch—$R^2$ | (5V) |
| $R^1$—Cy—Ph—CF=CF—C≡C—Ch—$R^2$ | (5W) |
| $R^1$—Ph—Ch—CF=CF—C≡C—Ch—$R^2$ | (5X) |
| $R^1$—Ch—Ph—CF=CF—C≡C—Ch—$R^2$ | (5Y) |
| $R^1$—Cy—Ch—CF=CF—C≡C—Ch—$R^2$ | (5Z) |
| $R^1$—Ch—Cy—CF=CF—C≡C—Ch—$R^2$ | (5a) |
| $R^1$—Ph—PhF—CF=CF—C≡C—Ph—$R^2$ | (5b) |
| $R^1$—Cy—PhF—CF=CF—C≡C—Ph—$R^2$ | (5c) |
| $R^1$—Ch—PhF—CF=CF—C≡C—Ph—$R^2$ | (5d) |
| $R^1$—Ph—PhF—CF=CF—C≡C—Cy—$R^2$ | (5e) |
| $R^1$—Cy—PhF—CF=CF—C≡C—Cy—$R^2$ | (5f) |
| $R^1$—Ch—PhF—CF=CF—C≡C—Cy—$R^2$ | (5g) |
| $R^1$—Ph—PhF—CF=CF—C≡C—Ch—$R^2$ | (5h) |
| $R^1$—Cy—PhF—CF=CF—C≡C—Ch—$R^2$ | (5i) |
| $R^1$—Ch—PhF—CF=CF—C≡C—Ch—$R^2$ | (5j) |

More specifically, the following compounds may be mentioned as the compound of the formula (6):

| | |
|---|---|
| $R^1$—Ph—CF=CF—C≡C—Ph—Ph—$R^2$ | (6A) |

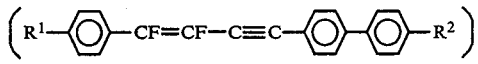

| | |
|---|---|
| $R^1$—Cy—CF=CF—C≡C—Cy—Cy—$R^2$ | (6B) |
| $R^1$—Ch—CF=CF—C≡C—Ch—Ch—$R^2$ | (6C) |
| $R^1$—Cy—CF=CF—C≡C—Ph—Ph—$R^2$ | (6D) |
| $R^1$—Ch—CF=CF—C≡C—Ph—Ph—$R^2$ | (6E) |
| $R^1$—Ph—CF=CF—C≡C—Cy—Cy—$R^2$ | (6F) |
| $R^1$—Ch—CF=CF—C≡C—Cy—Cy—$R^2$ | (6G) |
| $R^1$—Ph—CF=CF—C≡C—Ch—Ch—$R^2$ | (6H) |
| $R^1$—Cy—CF=CF—C≡C—Ch—Ch—$R^2$ | (6I) |
| $R^1$—Ph—CF=CF—C≡C—Ph—Cy—$R^2$ | (6J) |
| $R^1$—Ph—CF=CF—C≡C—Ph—Ch—$R^2$ | (6K) |
| $R^1$—Ph—CF=CF—C≡C—PhF—Ph—$R^2$ | (6L) |
| $R^1$—Ph—CF=CF—C≡C—PhF—Cy—$R^2$ | (6M) |
| $R^1$—Ph—CF=CF—C≡C—PhF—Ch—$R^2$ | (6N) |

Furthermore, the following compounds may be mentioned as compounds having three rings wherein $Y^1$ and $Y^2$ between rings are changed to other than a single bond:

| | |
|---|---|
| $R^1$—Ph—Ph—C≡C—Ph—CF=CF—C≡C—Ph—$R^2$ | (7A) |
| $R^1$—Ph—CH$_2$CH$_2$—Ph—CF=CF—C≡C—Ph—$R^2$ | (7B) |
| $R^1$—Ph—OCH$_2$—Ph—CF=CF—C≡C—Ph—$R^2$ | (7C) |
| $R^1$—Ph—CH$_2$O—Ph—CF=CF—C≡C—Ph—$R^2$ | (7D) |
| $R^1$—Ph—COO—Ph—CF=CF—C≡C—Ph—$R^2$ | (7E) |
| $R^1$—Ph—OCO—Ph—CF=CF—C≡C—Ph—$R^2$ | (7F) |
| $R^1$—Ph—C≡C—Ph—CF=CF—C≡C—Ph—$R^2$ | (7G) |
| $R^1$—Ph—CH$_2$CH$_2$—Ph—CF=CF—C≡C—Ph—$R^2$ | (7H) |
| $R^1$—Ph—OCH$_2$—Ph—CF=CF—C≡C—Ph—$R^2$ | (7I) |
| $R^1$—Ph—CH$_2$O—Ph—CF=CF—C≡C—Ph—$R^2$ | (7J) |
| $R^1$—Ph—COO—Ph—CF=CF—C≡C—Ph—$R^2$ | (7K) |
| $R^1$—Ph—OCO—Ph—CF=CF—C≡C—Ph—$R^2$ | (7L) |
| $R^1$—Ph—C≡C—Ph—CF=CF—C≡C—Ph—$R^2$ | (7M) |

R$^1$—Ph—CH$_2$CH$_2$—Ph—CF=CF—C≡C—Ph—R$^2$ (7N)

R$^1$—Ph—OCH$_2$—Ph—CF=CF—C≡C—Ph—R$^2$ (7O)

R$^1$—Ph—CH$_2$O—Ph—CF=CF—C≡C—Ph—R$^2$ (7P)

R$^1$—Ph—COO—Ph—CF=CF—C≡C—Ph—R$^2$ (7Q)

R$^1$—Ph—OCO—Ph—CF=CF—C≡C—Ph—R$^2$ (7R)

R$^1$—Ph—CF=CF—C≡C—Ph—C≡C—Ph—R$^2$ (7S)

R$^1$—Ph—CF=CF—C≡C—Ph—CH$_2$CH$_2$—Ph—R$^2$ (7T)

R$^1$—Ph—CF=CF—C≡C—Ph—OCH$_2$—Ph—R$^2$ (7U)

R$^1$—Ph—CF=CF—C≡C—Ph—CH$_2$O—Ph—R$^2$ (7V)

R$^1$—Ph—CF=CF—C≡C—Ph—COO—Ph—R$^2$ (7W)

R$^1$—Ph—CF=CF—C≡C—Ph—OCO—Ph—R$^2$ (7X)

Further, the following compound may be mentioned as compound having four rings:

R$^1$—A$^1$—A$^2$—CF=CF—C≡C—A$^3$—A$^4$—R$^2$ (8)

More specifically, the following compounds may be mentioned as the compound of the formula (8):

R$^1$—Ph—Ph—CF=CF—C≡C—Ph—Ph—R$^2$ (8A)

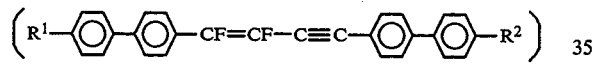

R$^1$—Cy—Cy—CF=CF—C≡C—Cy—Cy—R$^2$ (8B)

R$^1$—Ch—Ch—CF=CF—C≡C—Ch—Ch—R$^2$ (8C)

R$^1$—Cy—Ph—CF=CF—C≡C—Ph—Cy—R$^2$ (8D)

R$^1$—Ch—Ph—CF=CF—C≡C—Ph—Ch—R$^2$ (8E)

R$^1$—Ph—Cy—CF=CF—C≡C—Cy—Ph—R$^2$ (8F)

R$^1$—Ch—Cy—CF=CF—C≡C—Cy—Ch—R$^2$ (8G)

R$^1$—Ph—Ch—CF=CF—C≡C—Ch—Ph—R$^2$ (8H)

R$^1$—Cy—Ch—CF=CF—C≡C—Ch—Cy—R$^2$ (8I)

R$^1$—Ph—PhF—CF=CF—C≡C—PhF—Ph—R$^2$ (8J)

R$^1$—Cy—PhF—CF=CF—C≡C—PhF—Cy—R$^2$ (8K)

R$^1$—Ch—PhF—CF=CF—C≡C—PhF—Ch—R$^2$ (8L)

R$^1$—Ph—Ph—CF=CF—C≡C—Cy—Cy—R$^2$ (8M)

R$^1$—Ph—Ph—CF=CF—C≡C—Ch—Ch—R$^2$ (8N)

R$^1$—Cy—Cy—CF=CF—C≡C—Ch—Ch—R$^2$ (8O)

R$^1$—Cy—Ph—CF=CF—C≡C—Cy—Ph—R$^2$ (8P)

R$^1$—Ch—Ph—CF=CF—C≡C—Ch—Ph—R$^2$ (8Q)

R$^1$—Ch—Cy—CF=CF—C≡C—Ch—Cy—R$^2$ (8R)

Furthermore, the following compounds may be mentioned as compounds having four rings wherein Y$^1$ and Y$^2$ between rings are changed to other than a single bond;

R$^1$—Ph—C≡C—Ph—CF=CF—C≡C—Ph—Ph—R$^2$ (9A)

R$^1$—Ph—CH$_2$CH$_2$—Ph—CF=CF—C≡C—Ph—Ph—R$^2$ (9B)

R$^1$—Ph—OCH$_2$—Ph—CF=CF—C≡C—Ph—Ph—R$^2$ (9C)

R$^1$—Ph—CH$_2$O—Ph—CF=CF—C≡C—Ph—Ph—R$^2$ (9D)

R$^1$—Ph—COO—Ph—CF=CF—C≡C—Ph—Ph—R$^2$ (9E)

R$^1$—Ph—OCO—Ph—CF=CF—C≡C—Ph—Ph—R$^2$ (9F)

R$^1$—Ph—C≡C—Ph—CF=CF—C≡C—Ph—Cy—R$^2$ (9G)

R$^1$—Ph—CH$_2$CH$_2$—Ph—CF=CF—C≡C—Ph—Cy—R$^2$ (9H)

R$^1$—Ph—OCH$_2$—Ph—CF=CF—C≡C—Ph—Cy—R$^2$ (9I)

R$^1$—Ph—CH$_2$O—Ph—CF=CF—C≡C—Ph—Cy—R$^2$ (9J)

R$^1$—Ph—COO—Ph—CF=CF—C≡C—Ph—Cy—R$^2$ (9K)

R$^1$—Ph—OCO—Ph—CF=CF—C≡C—Ph—Cy—R$^2$ (9L)

R$^1$—Ph—C≡C—Ph—CF=CF—C≡C—Ph—Ch—R$^2$ (9M)

R$^1$—Ph—CH$_2$CH$_2$—Ph—CF=CF—C≡C—Ph—Ch—R$^2$ (9N)

R$^1$—Ph—OCH$_2$—Ph—CF=CF—C≡C—Ph—Ch—R$^2$ (9O)

R$^1$—Ph—CH$_2$O—Ph—CF=CF—C≡C—Ph—Ch—R$^2$ (9P)

R$^1$—Ph—COO—Ph—CF=CF—C≡C—Ph—Ch—R$^2$ (9Q)

R$^1$—Ph—OCO—Ph—CF=CF—C≡C—Ph—Ch—R$^2$ (9R)

R$^1$—Ph—Ph—CF=CF—C≡C—Ph—C≡C—Ph—R$^2$ (9S)

R$^1$—Ph—Ph—CF=CF—C≡C—Ph—CH$_2$CH$_2$—Ph—R$^2$ (9T)

R$^1$—Ph—Ph—CF=CF—C≡C—Ph—OCH$_2$—Ph—R$^2$ (9U)

R$^1$—Ph—Ph—CF=CF—C≡C—Ph—CH$_2$O—Ph—R$^2$ (9V)

R$^1$—Ph—Ph—CF=CF—C≡C—Ph—COO—Ph—R$^2$ (9W)

R$^1$—Ph—Ph—CF=CF—C≡C—Ph—OCO—Ph—R$^2$ (9X)

Further, the following compounds may be mentioned as examples in which some of hydrogen atoms of the 1,4-phenylene group, the trans-1,4-cyclohexylene group and the 1,4-cyclohexenylene group of $A^1$, $A^2$, $A^3$ and $A^4$ are substituted by halogen atoms or cyano groups, or some of =CH— groups constituting a ring are substituted by nitrogen atoms, or some of —CH$_2$— groups constituting a ring are substituted by oxygen atoms or sulfur atoms.

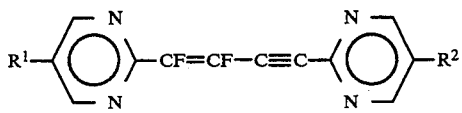

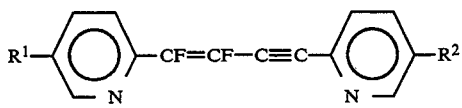

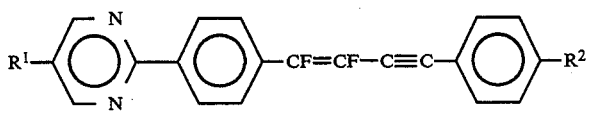

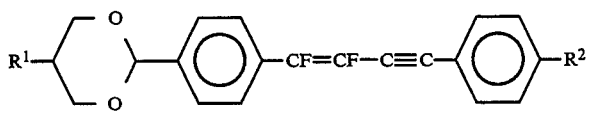

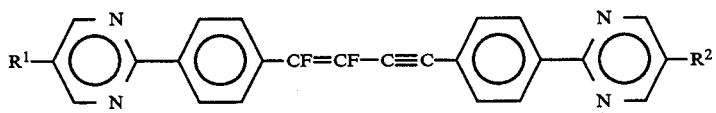

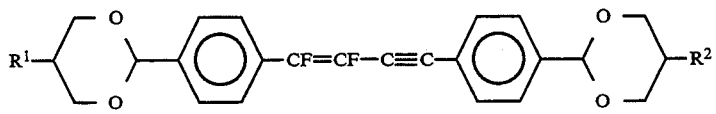

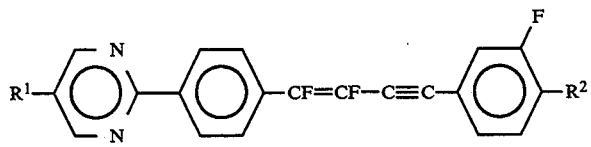

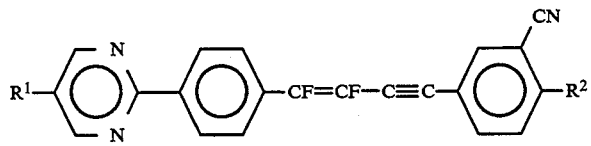

The compound of the formula (1) of the present invention is used in the form of a liquid crystal composition prepared by mixing at least one such compound with other liquid crystal material and/or a non-liquid crystal material, whereby the liquid crystal composition can be made to have a low viscosity, and it is possible to attain a high speed response when the composition is formed into a liquid crystal display device.

The material which may be mixed with the compound of the present invention, includes, for example, the following compounds. In the following formulas, each of $R^C$ and $R^D$ represents an alkyl group, an alkoxy group, halogen atom or a cyano group, provided that "—NON—" represents an azoxy group.

$R^c$—Cy—Cy—$R^D$
$R^c$—Cy—Ph—$R^D$
$R^c$—Ph—Ph—$R^D$
$R^c$—Cy—COO—Ph—$R^D$
$R^c$—Ph—COO—Ph—$R^D$
$R^c$—Cy—CH=CH—Ph—$R^D$
$R^c$—Ph—CH=CH—Ph—$R^D$
$R^c$—Cy—CH$_2$CH$_2$—Ph—$R^D$
$R^c$—Ph—CH$_2$CH$_2$—Ph—$R^D$
$R^c$—Ph—N=N—Ph—$R^D$
$R^c$—Ph—NON—Ph—$R^D$
$R^c$—Cy—COS—Ph—$R^D$
$R^c$—Cy—Ph—Ph—$R^D$ $R^c$—Cy—Ph—Ph—Cy—$R^D$
$R^c$—Ph—Ph—Ph—$R^D$
$R^c$—Cy—COO—Ph—Ph—$R^D$
$R^c$—Cy—Ph—COO—Ph—$R^D$
$R^c$—Cy—COO—Ph—COO—Ph—$R^D$
$R^c$—Ph—COO—Ph—COO—Ph—$R^D$
$R^c$—Ph—COO—Ph—OCO—Ph—$R^D$

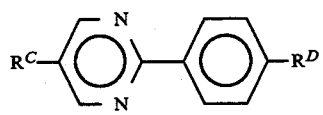

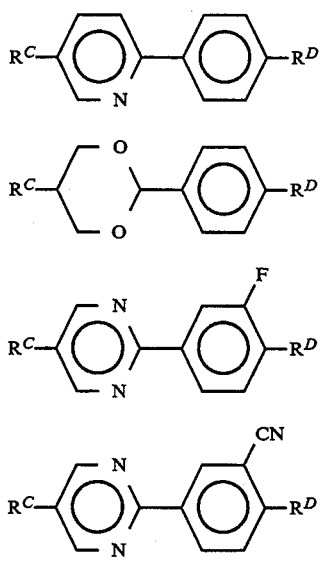

These compounds are given merely as examples. The ring structures or hydrogen atoms of the terminal groups may be substituted by halogen atoms, cyano groups or methyl groups, and the cyclohexane rings or the benzene rings may be replaced by other six-membered or five-membered rings such as pyridine rings or dioxane rings. Further, the linking group between the adjacent rings may be changed. Thus, various materials may be approximately selected for use depending upon the desired properties.

The liquid crystal composition containing the compound of the present invention may be injected into a liquid crystal cell, so that it is interposed between substrates provided with electrodes, to constitute a liquid crystal electro-optical device.

A typical liquid crystal cell may be a twisted nematic (TN) type liquid crystal electro-optical device. Here, the term "liquid crystal electro-optical device" is used to express that it is useful not only for application to a display device but also to e.g. a light adjustable window, a light shutter or a polarizing exchanger device.

The liquid crystal electro-optical device can be used in various modes such as a twisted nematic system, a guest-host system, a dynamic scattering system, a phase change system, a DAP system, a double frequency drive system and a ferroelectric liquid crystal display system.

Now, a structure of a liquid crystal electro-optical device and a specific example for the preparation will be described.

On a substrate made of a plastic, glass or the like, an undercoat layer of $SiO_2$, $Al_2O_3$ or the like, or a color filter layer is formed as the case requires, and then an electrode for $In_2O_3$-$SnO_2$ (ITO), $SnO_2$ or the like is formed thereon, followed by patterning. Then, an overcoat layer of polyimide, polyamide, $SiO_2$ or $Al_2O_3$ is formed as the case requires, followed by orientation treatment. Then, a sealing material is printed, and the periphery is sealed so that the electrode surfaces face to each other, followed by curing the sealing material to form an empty cell.

To this empty cell, the composition containing the compound of the present invention is injected, and the injection inlet is then sealed with a sealing agent to form a liquid crystal cell. To this liquid crystal cell, a polarizing plate, a color polarizing plate, a light source, a color filter, a semitransparent reflecting plate, a reflecting plate, a photoconducting plate, an ultraviolet ray-preventive filter or the like may be laminated, letters or designs may be printed, and nonglare treatment may be applied as the case requires, to obtain a liquid crystal electro-optical device.

The above description is intended to show merely the basic structure and the basic method for preparation of a liquid crystal electro-optical device. Various other structures may be employed, including, for example, a double layer liquid crystal cell having two liquid crystal layers with a substrate employing double layer electrodes, and an active matrix device using an active matrix substrate having a functional element such as TFT or MIM formed thereon.

By using the compound of the present invention for a liquid crystal composition, high speed response can be expected also by conducting high duty drive. Therefore, the present invention is effectively applicable to a supertwisted (STN) type liquid crystal electro-optical device having a highly twisted angle, to which an attention has been drawn in recent years. Further, the present invention is useful also for a guest-host (GH) type liquid crystal display device using multicolor colorants or a ferroelectric liquid crystal electro-optical device.

The compound of the formula (1) of the present invention can be produced, for example, by the following method.

$$CF_2=CFCl \quad (10)$$
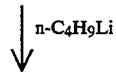
$$Cl-Si(CH_3)_3 \quad (11)$$
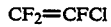
$$CF_2=CFCl \quad (12)$$
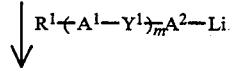
$$R^1-(A^1-Y^1)_{\overline{m}}A^2-Li \quad (13)$$
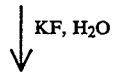
$$R^1-(A^1-Y^1)_{\overline{m}}A^2-CF=CF-Si(CH_3)_3 \quad (14)$$
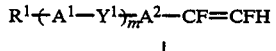
$$R^1-(A^1-Y^1)_{\overline{m}}A^2-CF=CFH \quad (15)$$
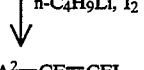
$$R^1-(A^1-Y^1)_{\overline{m}}A^2-CF=CFI \quad (16)$$
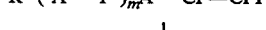
$$R^2-(A^4-Y^2)_{\overline{n}}A^3-C\equiv CH \quad (17)$$
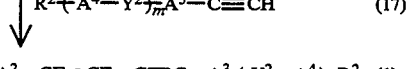
$$R^1-(A^1-Y^1)_{\overline{m}}A^2-CF=CF-C\equiv C-A^3-(Y^2-A^4)_{\overline{n}}R^2 \quad (1)$$

In the above formulas, each of $A^1$, $A^2$, $A^3$ and $A^4$, which are independent from one another, is a cyclic group selected from a trans-1,4-cyclohexylene group, a 1,4-cyclohexenylene group and a 1,4-phenylele group. Each of these cyclic groups is unsubstituted or substituted by one or more halogen atoms or cyano groups. One or more =CH— groups constituting rings of such cyclic groups may be substituted by nitrogen atoms, and one or more —CH$_2$— groups constituting such rings may be substituted by oxygen atoms or sulfur atoms.

Each of Y$^1$ and Y$^2$ which are independent from each other, is —COO—, —OCO—, —C≡C—, —CH$_2$CH$_2$—, —CH═CH—, —OCH$_2$—, —CH$_2$O— or a single bond.

Each of m and n, which are independent from each other, is 0 or 1.

Each of R$^1$ and R$^2$, which are independent from each other, is a C$_{1-10}$ alkyl group, a halogen atom or a cyano group. In the case of an alkyl group, an oxygen atom, a carbonyloxy group or an oxycarbonyl group may be interposed in a carbon-carbon bond in this alkyl group or in the carbon-carbon bond between this alkyl group and the cyclic group. Further, some of carbon-carbon bonds in the alkyl group may be triple bonds or double bonds. Furthermore, one —CH$_2$— group in the alkyl group may be substituted by a carbonyl group, and some or all of hydrogen atoms in the alkyl group may be substituted by fluorine atoms.

X is a bromine atom or an iodine atom.

Chlorotrifluoroethylene of the formula (10) is treated with n-butyl lithium and then reacted with chlorotrimethylsilane of the formula (11) to obtain 1,1,2-trifluoro-2-trimethylsilylethylene of the formula (12). Then, without isolation, this compound (12) is reacted further with a lithium compound of the formula (13) to obtain a difluoroethylene compound of the formula (14).

The obtained compound (14) is hydrolyzed with water and potassium fluoride to obtain a difluoroethylene compound of the formula (15). This compound is treated with n-butyl lithium and then reacted with iodine to obtain an iodide compound of the formula (16). Further, an acetylene derivative compound of the formula (17) is reacted thereto in the presence of a palladium catalyst, copper iodide and triethylamine to obtain a difluoro compound of the formula (1).

To introduce an acyl group to R$^1$ and R$^2$ of the compound of the formula (1), a compound of the formula (1) wherein R$^1$ and R$^2$ are hydrogen atoms and an acyl halide may be subjected to a Friedel-Crafts reaction. To introduce a cyano group, a compound of the formula (1) wherein R$^1$ and R$^2$ are bromine atoms or iodine atoms may be reacted with CuCN. Further, to introduce an ethynylene group (—C≡C—) to Y$^1$ and Y$^2$ of the compound of the formula (1), a compound of the formula (1) wherein R$^1$ and R$^2$ are bromine atoms or iodine atoms and an alkynyl lithium compound may be subjected to a coupling reaction.

BEST MODE FOR CARRYING OUT THE INVENTION

EXAMPLE 1

First step

Into a 500 ml of three-necked flask equipped with a condenser and a gas supply tube, 100 ml of tetrahydrofuran (THF) was charged and cooled to −100° C. Then, 11.7 g (0.1 mol) of chlorotrifluoroethylene was introduced thereto. 62.1 ml (0.1 mol) of a n-hexane solution of n-butyl lithium (1.61M) was dropwise added thereto over a period of 30 minutes. The mixture was stirred for further 30 minutes, and then 10.9 g (0.1 mol) of chlorotrimethylsilane was dropwise added thereto.

After the dropwise addition, the mixture was stirred for one hour. Then, a THF solution of 4-propylphenyl lithium separately synthesized by 24.6 g (0.1 mol) of 4-propyl iodobenzene and 62.1 ml (0.1 mol) of a n-hexane solution of n-butyl lithium (1.61M), was dropwise added thereto at −100° C. The mixture was further stirred for two hours at 0° C. Then, a dilute hydrochloric acid aqueous solution was added thereto. The organic layer was separated. The aqueous layer was extracted with methylene chloride, and the organic layers were put together and dried. Then, the solvent was distilled off to obtain 19.1 g (yield: 75%) of (Z)-1,2-difluoro-1-(4-propylphenyl)-2-trimethylsilyl ethylene.

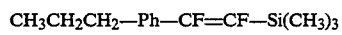

Second step

Then, 19.1 g (0.075 mol) of the obtained (Z)-1,2-difluoro-1-(4-n-propylphenyl)-2-trimethylsilylethylene was dissolved in 50 ml of acetonitrile, and then 8.70 g (0.15 mol) of potassium fluoride and 4.05 g (0.225 mol) of water were added thereto. The mixture was reacted for one hour at 70° C. The reaction mixture was cooled, and then 200 ml of water was added thereto. The mixture was extracted with methylene chloride. The organic layer was washed with a saturated sodium chloride aqueous solution and dried over CaCl$_2$. After filtration, the solvent and low boiling substances were distilled off, and the residue was further distilled under reduced pressure to obtain 11.3 g (yield: 83%) of (E)-1,2-difluoro-1-(4-propylphenyl)ethylene.

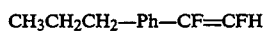

Third step

Then, 11.3 g (0.062 mol) of the obtained (E)-1,2-difluoro-1-(4-propylphenyl)ethylene was dissolved in 50 ml of THF, and the solution was cooled to −78° C. Then, 38.5 ml (0.062 mol) of a n-hexane solution of n-butyl lithium (1.61M) was dropwise added thereto over a period of 30 minutes. The mixture was stirred for further 30 minutes, and then 15.7 g (0.062 mol) of iodide was added at −78° C.

The mixture was heated to room temperature and stirred for 4 hours, and then a sodium thiosulfate aqueous solution was added thereto. The organic layer was separated. The aqueous layer was extracted with methylene chloride, and the organic layers were put together and dried. Then, the solvent was distilled off, and the obtained crude oil was distilled under reduced pressure to obtain 15.8 g (yield: 83%) of (E)-1,2-difluoro-1-iodo-2-(4-propylphenyl)ethylene.

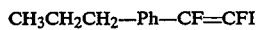

Fourth step

Then, 15.8 g (0.051 mol) of the obtained (E)-1,2-difluoro-1-iodo-2-(4-propylphenyl)ethylene and 7.34 g (0.051 mol) of 4-propylphenyl acetylene were dissolved in ml of triethylamine, and 0.7 g of Pd(PPh$_3$)$_2$Cl$_2$ and 0.2 g of CuI were further added thereto.

The mixture was reacted at room temperature for 6 hours.

After the reaction, triethylamine was distilled off, and 100 ml of methylene chloride was added. The mixture was washed with a 5% hydrochloric acid aqueous solution and then with water and dried. Then, the solvent was distilled off. The obtained solid was purified by silica gel column chromatography to obtain 11.6 g (yield: 70%) of (E)-3,4-difluoro-1,4-bis(4-propylphenyl)-3-buten-1-yne.

CH₃CH₂CH₂—Ph—CF=CF—C≡C—
Ph—CH₂CH₂CH₃

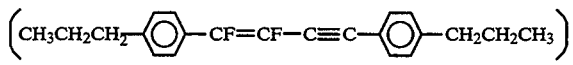

The analytical results of this compound will be shown below.

| ¹⁹F NMR(CDCl₃) δppm from CFCl₃ | −145.2 ppm (d, $J_{F-F}$ = 134Hz) |
|---|---|
| | −148.4 ppm (d, $J_{F-F}$ = 134Hz) |
| MS | m/e 324(M⁺) |
| IR | 1160 cm⁻¹ (C—F) |

In the same manner as in Example 1, the following compounds can be prepared. Here, "—Ph—F" represents a p-fluorophenyl group.
CH₃—Ph—CF=CF—C≡C—Ph—CH₃
CH₃CH₂CH₂CH₂CH₂—Ph—CF=CF—C≡C—
Ph—CH₂CH₂CH₂CH₃
CF₃—Ph—CF=CF'C≡C—Ph—CF₃
F—Ph—CF=CF—C≡C—Ph—F
CH₃O—Ph—CF=CF—C≡C—Ph—OCH₃
CH₃CH₂CH₂O—Ph—CF=CF—C≡C—
Ph—OCH₂CH₂CH₃
CH₂=CH—Ph—CF=CF—C≡C—Ph—CH=CH₂

EXAMPLE 2

The reactions were conducted in the same manner as in Example 1 except that in the first step in Example 1, 20.5 g (0.1 mol) of 4-propylcyclohexyl bromide was used instead of 4-propyliodobenzene, to obtain 11.6 g (yield: of (E)-3,4-difluoro-1-(4-propylphenyl)-4-(4-propylcyclohexyl)-3-buten-1-yne.

CH₃CH₂CH₂—Cy—CF=CF—C≡C—
Ph—CH₂CH₂CH₃

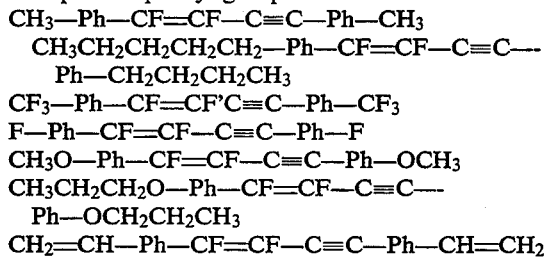

The analytical results of this compound will be shown below.

| MS | m/e 330(M⁺) |
|---|---|
| IR | 1160 cm⁻¹ (C—F) |

In the same manner as in Example 2, the following compounds can be prepared.
CH₃—Cy—CF=CF—C≡C—Ph—CH₃
CH₃CH₂CH₂CH₂CH₂—Cy—CF=CF—C≡C—
Ph—CH₂CH₂CH₂CH₂CH₃
CF₃—Cy—CF=CF—C≡C—Ph—CF₃
F—Cy—CF=CF—C≡C—Ph—F
CH₃O—Cy—CF=CF—C≡C—Ph—OCH₃
CH₃CH₂CH₂O—Cy—CF=CF—C≡C—
Ph—OCH₂CH₂CH₃
CH₂=CH—Cy—CF=CF—C≡C—Ph—CH=CH₂

EXAMPLE 3

The reactions were conducted in the same manner as in Example 1 except that in the first step of Example 1, 25.0 g (0.1 mol) of 4-propylcyclohexene-1-iodo-1-yl was used instead of 4-propyliodobenzene, to obtain 9.8 g (yield: 30%) of (E)-3,4-difluoro-1-(4-propylphenyl)-4-(4-propylcyclohexen-1-yl)-3-buten-1-yne.

CH₃CH₂CH₂—Ch—CF=CF—C≡C—
Ph—CH₂CH₂CH₃

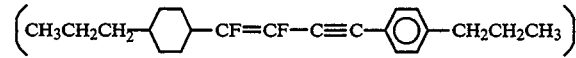

The analytical results of this compound will be shown below.

| MS | m/e 328(M⁺) |
|---|---|
| IR | 1160 cm⁻¹ (C—F) |

In the same manner as in Example 3, the following compounds can be prepared.
CH₃—Ch—CF=CF—C≡C—Ph—CH₃
CH₃CH₂CH₂CH₂CH₂—Ch—CF=CF—C≡C—
Ph—CH₂CH₂CH₂CH₃
CF₃—Ch—CF=CF—C≡C—Ph—CF₃
F—Ch—CF=CF—C≡C—Ph—F
CH₃O—Ch—CF=CF—C≡C—Ph—OCH₃
CH₃CH₂CH₂O—Ch—CF=CF—C≡C—
Ph—OCH₂CH₂CH₃
CH₂=CH—Ch—CF=CF—C≡C—Ph—CH=CH₂

EXAMPLE 4

The reactions were conducted in the same manner as in Example 1 except that in the first step of Example 1, 23.6 g (0.1 mol) of 1,4-dibromobenzene was used instead of the 4-propyliodobenzene, to obtain 13.7 g (yield: 38%) of (E)-3,4-difluoro-1-(4-propylphenyl)-4-(4-bromophenyl)-3-buten-1-yne.

Br—Ph—CF=CF—C≡C—Ph—CH₂CH₂CH₃

The analytical results of this compound will be shown below.

| MS | m/e 361(M⁺) |
|---|---|
| IR | 1160 cm⁻¹ (C—F) |

In the same manner as in Example 4, the following compounds can be prepared.
Br—Cy—CF=CF—C≡C—Ph—CH₂CH₂CH₃
Br—Ch—CF=CF—C≡C—Ph—CH₂CH₂CH₃

EXAMPLE 5

Into a 300 ml three-necked flask equipped with a condenser, 0.90 g (0.01 mol) of CuCN and 50 ml of dry dimethylsulfoxide (DMSO) were introduced, heated to 90° C. and dissolved. Then, a DMSO solution containing 3.61 g (0.01 mol) of (E)-3,4-difluoro-1-(4-propylphenyl)-4-(4-bromophenyl)-3-buten-1-yne obtained in Example 4, was dropwise added thereto under stirring.

Then, the mixture was stirred for further one hour at 150° C. and then cooled to room temperature.

200 ml of water was poured thereto. The mixture was extracted with methylene chloride, and the organic layer was washed with a saturated sodium chloride aqueous solution and dried over $CaCl_2$. After filtration, the solvent was distilled off, and the obtained solid was purified by silica gel column chromatography to obtain 2.52 g (yield: 82%) of (E)-3,4-difluoro-1-(4-propylphenyl)-4-(4-cyanophenyl)-3-buten-1-yne.

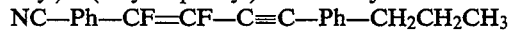

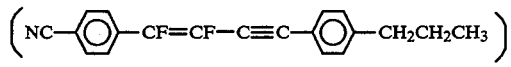

The analytical results of this compound will be shown below.

| MS | m/e 307(M+) |
| --- | --- |
| IR | 1160 cm$^{-1}$ (C—F), 2230 cm$^{-1}$ (C≡N) |

In the same manner as in Example 5, the following compounds can be prepared. NC—Cy—CF=CF—C≡C—Ph—CH$_2$CH$_2$CH$_3$
NC—Ch—CF=CF—C≡C—Ph—CH$_2$CH$_2$CH$_3$

EXAMPLE 6

The reactions were conducted in the same manner as in Example 1 except that in the first step of Example 1, 17.5 g (0.1 mol) of 5-methylpyrimidyl bromide was used instead of 4-propyliodobenzene, to obtain 9.54 g (yield: 32%) of (E)-3,4-difluoro-1-(4-propylphenyl)-4-(5-methylpyrimidin-2-yl)-3-buten-1-yne.

The analytical results of this compound will be shown below.

| MS | m/e 298(M+) |
| --- | --- |
| IR | 1160 cm$^{-1}$ (C—F) |

In the same manner as in Example 6, the following compounds can be prepared. Here, "—Py—" represents a pyrimidin-2,5-diyl group.
CH$_3$CH$_2$CH$_2$—Py—CF=CF—C≡C—Ph—CH$_2$CH$_2$CH$_3$
CH$_3$O—Py—CF=CF—C≡C—Ph—CH$_2$CH$_2$CH$_3$
CH$_3$CH$_2$CH$_2$O—Py—CF=CF—C≡C—Ph—CH$_2$CH$_2$CH$_3$

EXAMPLE 7

The reactions were conducted in the same manner as in Example 1 except that in the first step of Example 1, 18.1 g (0.1 mol) of 2-methyl-5-bromo-1,3-dioxane was used instead of 4-propyliodobenzene, to obtain 9.18 g (yield: of (E)-3,4-difluoro-1-(4-propylphenyl)-4-(5-methyl-1,3-dioxan-2-yl)-3-buten-1-yne. Further, in the following description, "—Do—" represents a 1,3-dioxan-2-5-diyl group.

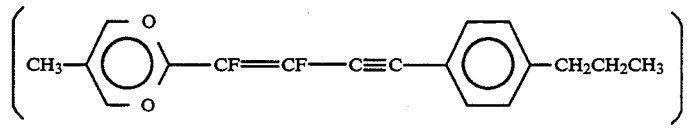

The analytical results of this compound will be shown below.

| MS | m/e 306(M+) |
| --- | --- |
| IR | 1160 cm$^{-1}$ (C—F) |

In the same manner as in Example 7, the following compounds can be prepared.
CH$_3$CH$_2$CH$_2$—Do—CF=CF—C≡C—Ph—CH$_2$CH$_2$CH$_3$
CH$_3$O—Do—CF=CF—C≡C—Ph—CH$_2$CH$_2$CH$_3$
CH$_3$CH$_2$CH$_2$O—Do—CF=CF—C≡C—Ph—CH$_2$CH$_2$CH$_3$

EXAMPLE 8

The reactions were conducted in the same manner as in Example 1 except that in the first step of Example 1, 32.8 g (0.1 mol) of 4-(trans-4-propylcyclohexyl)iodobenzene was used instead of 4-propyliodobenzene, to obtain 14.6 g (yield: 36%) of (E)-3,4-difluoro-4-[4-(trans-4-propylcyclohexyl)phenyl]-1-(4-propylphenyl)-3-buten-1-yne.

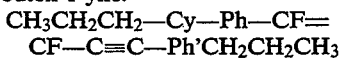

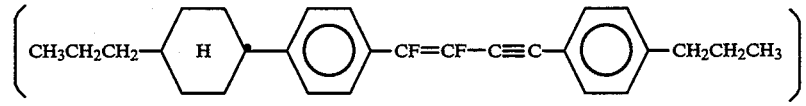

The analytical results of this compound will be shown below.

| MS | m/e 406(M+) |
|---|---|
| IR | 1160 cm$^{-1}$ (C—F) |

In the same manner as in Example 8, the following compounds can be prepared.
CH$_3$CH$_2$CH$_2$—Ph—Ph—CF=CF—C≡C—Ph—CH$_2$CH$_2$CH$_3$
CH$_3$CH$_2$CH$_2$—Ph—Cy—CF=CF—C≡C—Ph—CH$_2$CH$_2$CH$_3$
CH$_3$CH$_2$CH$_2$—Cy—Cy—CF=CF—C≡C—Ph—CH$_2$CH$_2$CH$_3$
CH$_3$CH$_2$CH$_2$—Ph—Ch—CF=CF—C≡C—Ph—CH$_2$CH$_2$CH$_3$
CH$_3$CH$_2$CH$_2$—Ch—Ph—CF=CF—C≡C—Ph—CH$_2$CH$_2$CH$_3$
CH$_3$CH$_2$CH$_2$—Ch—Ch—CF=CF—C≡C—Ph—CH$_2$CH$_2$CH$_3$

EXAMPLE 9

The reactions were conducted in the same manner as in Example 1 except that in the fourth step of Example 1, 4-propylcyclohexylacetylene was used instead of 4-propylphenylacetylene, to obtain 8.25 g (yield: 25%) of (E)-3,4-difluoro-1-(4-propylcyclohexyl)-4-(4-propylphenyl)-3-buten-1-yne.

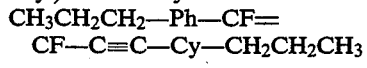

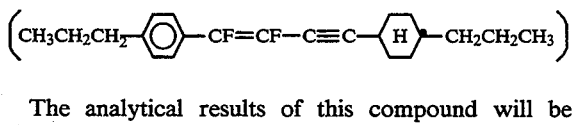

The analytical results of this compound will be shown below.

| MS | m/e 330(M+) |
|---|---|
| IR | 1160 cm$^{-1}$ (C—F) |

In the same manner as in Example 9, the following compounds can be prepared.
CH$_3$—Ph—CF=CF—C≡C—Cy—CH$_2$CH$_2$CH$_3$
CH$_3$CH$_2$CH$_2$CH$_2$CH$_2$—Ph—CF=CF—C≡C—Cy—CH$_2$CH$_2$CH$_3$
CF$_3$—Ph—CF=CF—C≡C—Cy—CH$_2$CH$_2$CH$_3$
F—Ph—CF=CF—C≡C—Cy—CH$_2$CH$_2$CH$_3$
CH$_3$O—Ph—CF=CF—C≡C—Cy—CH$_2$CH$_2$CH$_3$
CH$_3$CH$_2$CH$_2$O—Ph—CF=CF—C≡C—Cy—CH$_2$CH$_2$CH$_3$
CH$_2$=CH—Ph—CF=CF—C≡C—Cy—CH$_2$CH$_2$CH$_3$
CH$_3$—Ph—CF=CF—C≡C—Ch—CH$_2$CH$_2$CH$_3$
CH$_3$CH$_2$CH$_2$CH$_2$CH$_2$—Ph—CF=CF—C≡C—Ch—CH$_2$CH$_2$CH$_3$
CF$_3$—Ph—CF=CF—C≡C—Ch—CH$_2$CH$_2$CH$_3$
F—Ph—CF=CF—C≡CF—Ch—CH$_3$CH$_2$CH$_2$
CH$_3$O—Ph—CF=CF—C≡C—Ch—CH$_2$CH$_2$CH$_3$
CH$_3$CH$_2$CH$_2$O—Ph—CF=CF—C≡C—Ch—CH$_2$CH$_2$CH$_3$
CH$_2$=CH—Ph—CF=CF—C≡C—Ch—CH$_2$CH$_2$CH$_3$

EXAMPLE 10

The reactions were conducted in the same manner as in Example 1 except that in the first step of Example 1, 20.5 9 (0.1 mol) of 4-propylcyclohexyl bromide was used instead of 4-propyliodobenzene, and in the fourth step, 4-propylcyclohexylacetylene was used instead of the 4-propylphenylacetylene, to obtain 7.39 9 (yield: 22%) of (E)-3,4-difluoro-1,4-bis(4-propylcyclohexyl)-3-buten-1-yne.

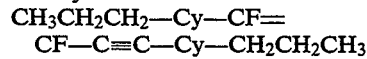

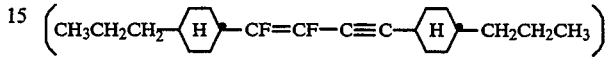

The analytical results of this compound will be shown below.

| MS | m/e 336(M+) |
|---|---|
| IR | 1160 cm$^{-1}$ (C—F) |

In the same manner as in Example 10, the following compounds can be prepared.
CH$_3$—Cy—CF=CF—C≡C—Cy—CH$_2$—CH$_2$CH$_3$
CH$_3$CH$_2$CH$_2$CH$_2$CH$_2$—Cy—CF=CF—C≡C—Cy—CH$_2$CH$_2$CH$_3$
CF$_3$—Cy—CF=CF—C≡C—Cy—CH$_2$CH$_2$CH$_3$
F—Cy—CF=CF—C≡C—Cy—CH$_2$CH$_2$CH$_3$
CH$_3$O—Cy—CF=CF—C≡C—Cy—CH$_2$CH$_2$CH$_3$
CH$_3$CH$_2$CH$_2$O—Cy—CF=CF—C≡C—Cy—CH$_2$CH$_2$CH$_3$
CH$_2$=CH—Cy—CF=CF—C≡C—Cy—CH$_2$CH$_2$CH$_3$
CH$_3$—Ch—CF=CF—C≡C—Ch—CH$_2$CH$_2$CH$_3$
CH$_3$CH$_2$CH$_2$CH$_2$CH$_2$—Ch—CF=CF—C≡C—Ch—CH$_2$CH$_2$CH$_3$
CF$_3$—Ch—CF=CF—C≡C—Ch—CH$_2$CH$_2$CH$_3$
F—Ch—CF=CF—C≡C—Ch—CH$_2$CH$_2$CH$_3$
CH$_3$O—Ch—CF=CF—C≡C—Ch—CH$_2$CH$_2$CH$_3$
CH$_3$CH$_2$CH$_2$O—Ch—CF=CF—C≡C—Ch—CH$_2$CH$_2$CH$_3$
CH$_2$=CH—Ch—CF=CF—C≡C—Ch—CH$_2$CH$_2$CH$_3$

EXAMPLE 11

Into a 100 ml three-necked flask equipped with a reflux condenser, 0.13 9 (0.0055 mol) of magnesium and 10 ml of dry THF were introduced under an argon atmosphere. Then, a few drops of 1-bromopropane was added thereto, and 1.019 (0.0055 mol) of 4-methylphenethyl bromide was further dropwise added at a rate where heat generation continued. After completion of the dropwise addition, the mixture was refluxed for further one hour and then left to cool to room temperature.

Separately, into a 100 ml three-necked flask equipped with a refluxed condenser, 1.81 9 (0.005 mol) of (E)-3,4-difluoro-1-(4-propylphenyl)-4-(4-bromophenyl)-3-buten-1-yne obtained in Example 4 and 20 ml of a dry THF solution containing 0.19 of 1,3-bis(diphenylphosphino)propanedichloronickel [NiCl$_2$ (dppp)] were introduced under an argon atmosphere, and the above solution was dropwise added thereto by means of a dropping funnel.

After the dropwise addition, the mixture was stirred at room temperature for 24 hours. Then, 20 ml of water was added thereto. Further, 20 ml of 20% hydrochloric acid was added. Then, the organic layer was separated, washed with water and dried, and then the solvent was distilled off. The obtained crude product was purified by silica gel column chromatography to obtain 0.90 g (yield: 45%) of (E)-3,4-difluoro-1-(4-propylphenyl)-4-[4-(4-methylphenethyl)phenyl]-3-buten-1-yne.

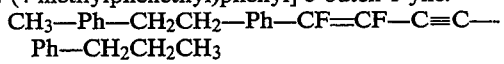

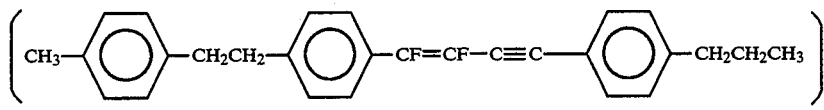

The analytical results of this compound will be shown below.

| MS | m/e 400(M+) |
|---|---|
| IR | 1160 cm$^{-1}$ (C—F) |

In the same manner as in Example 11, the following compounds can be prepared.

CH$_3$—Ph—CH$_2$CH$_2$—Cy—CF=CF—C≡C—Ph—CH$_2$CH$_2$CH$_3$
CH$_3$—Ph—CH$_2$CH$_2$—Ch—CF=CF—C≡C—Ph—CH$_2$CH$_2$CH$_3$
CH$_3$O—Ph—CH$_2$CH$_2$—Ph—CF=CF—C≡C—Ph—CH$_2$CH$_2$CH$_3$

EXAMPLE 12

The reactions were conducted in the same manner as in Example 11 except that in Example 11, 1.08 g (0.0055 mol) of 1-bromo-2-(4-methylphenyl)ethene was used instead of 4-methylphenethyl bromide, to obtain 1.00 g (yield: 50%) of (E)-3,4-difluoro-1-(4-propylphenyl)-4-[4-(2-p-methylphenylethenyl)phenyl]-3-buten-1-yne.

CH$_3$—Ph—CH=CH—Ph—CF=CF—C≡C—Ph—CH$_2$CH$_2$CH$_3$

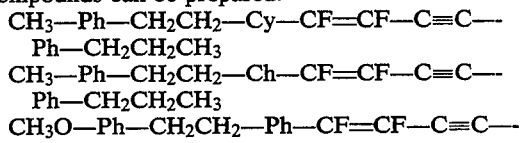

The analytical results of this compound will be shown below.

| MS | m/e 398(M+) |
|---|---|
| IR | 1160 cm$^{-1}$ (C—F) |

In the same manner as in Example 12, the following compounds can be prepared.

CH$_3$—Ph—CH=CH—Cy—CF=CF—C≡C—Ph—CH$_3$
CH$_3$—Ph—CH=CH—Ch—CF=CF—C≡C—Ph—CH$_3$
CH$_3$O—Ph—CH=CH—Ph—CF=CF—C≡C—Ph—OCH$_3$

EXAMPLE 13

Into a 100 ml three-necked flask, 2.86 g of cuprous iodide, 4.33 g (0.012 mol) of (E)-3,4-difluoro-1-(4-propylphenyl)-4-(4-bromophenyl)-3-buten-1-yne obtained in Example 4 and 30 ml of dry THF were charged under an argon atmosphere, followed by stirring at room temperature. Then, 1.42 g of n-butylamine and 1.53 g of p-toluylacetylene were added thereto. Then, 10 ml of a dry THF solution containing 0.69 g of (Ph$_3$P)$_4$Pd was added thereto, and the mixture was stirred at room temperature for 2 hours. After an addition of 30 ml of a saturated NaHCO$_3$ aqueous solution, the mixture was subjected to liquid separation, and then extracted with methylene chloride. The solvent was distilled off, and the residue was purified by silica gel column chromatography to obtain 3.09 g (yield: 65%) of (E)-3,4-difluoro-1-(4-propylphenyl)-4-[4-(2-p-toluylethynyl)phenyl]-3-buten-1-yne.

CH$_3$—Ph—C≡C—Ph—CF=CF—C≡C—Ph—CH$_2$CH$_2$CH$_3$

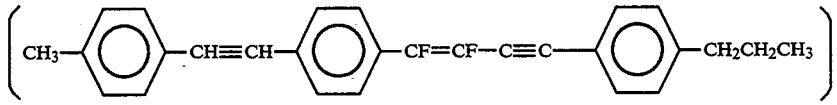

The analytical results of this compound will be shown below.

| MS | m/e 396(M+) |
|---|---|
| IR | 1160 cm$^{-1}$ (C—F) |

In the same manner as in Example 13, the following compounds can be prepared.

CH$_3$—Ph—C≡C—Cy—CF=CF—C≡C—Ph—CH$_2$CH$_2$CH$_3$
CH$_3$—Ph—C≡C—Ch—CF=CF—C≡C—Ph—CH$_2$CH$_2$CH$_3$
CH$_3$O—Ph—C≡C—Ph—CF=CF—C≡C—Ph—CH$_2$CH$_2$CH$_3$

EXAMPLE 14

The reactions were conducted in the same manner as in Example 1 except that in the first step of Example 1, 30.4 9 (0.1 mol) of 4-iodophenyltetrahydropyranyl ether was used instead of 4-propyliodobenzene, and the product was finally treated with an acid, to obtain 8.05 (yield: 27%) of (E)-3,4-difluoro-4-(4-hydroxylphenyl)-1-(4-propylphenyl)-3-buten-1-yne.

HO—Ph—CF=CF—C≡C—Ph—CH₂CH₂CH₃

Then, 1.49 g (0.005 mol) of the obtained (E)-3,4-difluoro-4-(4-hydroxyphenyl)-1-(4-propylphenyl)-3-buten-1-yne, 1.52 g of potassium carbonate and 30 ml of acetone were added. Further, 2.79 g of α-bromo-p-xylene was dropwise added thereto at room temperature. The mixture was refluxed for 4 hours, then cooled and filtered. Then, the solvent was distilled off, and the obtained crude crystals were purified by silica gel column chromatography to obtain 1.71 g (yield: 85%) of (E)-3,4-difluoro-4-[4-(4-methylbenzyloxy)phenyl-1-(4-propylphenyl)-3-buten-1-yne.

CH₃—Ph—CH₂O—Ph—CF=CF—C≡C—Ph—CH₂CH₂CH₃

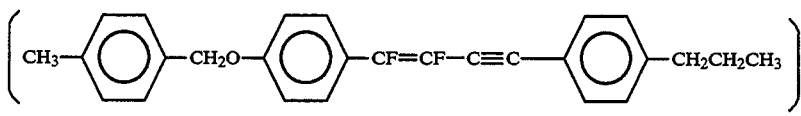

The analytical results of this compound will be shown below.

| MS | m/e 402(M⁺) |
|---|---|
| IR | 1160 cm⁻¹ (C—F) |

In the same manner as in Example 14, the following compounds can be prepared.
CH₃—Ph—CH₂O—Cy—CF=CF—C≡C—Ph—CH₃CH₂CH₂
CH₃—Ph—CH₂O—Ch—CF=CF—C≡C—Ph—CH₃CH₂CH₂
CH₃O—Ph—CH₂O—Ph—CF=CF—C≡C—Ph—CH₂CH₂CH₃

EXAMPLE 15

1.49 g (0.005 mol) of (E)-3,4-difluoro-4-(4-hydroxyphenyl)-1-(4-propylphenyl)-3-buten-1-yne obtained in Example 14 was dissolved in 20 ml of CH₂Cl₂, and 0.87 g of pyridine was added thereto at room temperature. The mixture was cooled to 0° C., and then 1.70 g of p-toluic acid chloride was dropwise added thereto.

The mixture was stirred at room temperature for one hour and cooled, and then dilute hydrochloric acid was added thereto, followed by filtration. Then, the solvent was distilled off, and the obtained crude crystals were purified by silica gel column chromatography to obtain 1.87 g (yield: 90%) of (E)-3,4-difluoro-4-[4-(4-methylbenzoyloxy)]-1-(4-propylphenyl)-3-buten-1-yne.

CH₃—Ph—COO—Ph—CF=CF—C≡C—Ph—CH₂CH₂CH₃

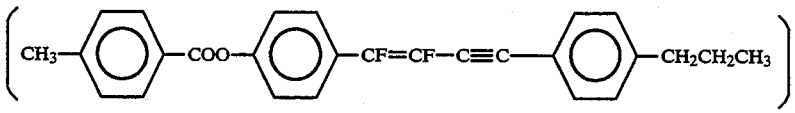

The analytical results of this compound will be shown below.

| MS | m/e 416(M⁺) |
|---|---|
| IR | 1160 cm⁻¹ (C—F), 1720 cm⁻¹ (C=O) |

In the same manner as in Example 15, the following compounds can be prepared.
CH₃—Ph—COO—Cy—CF=CF—C≡C—Ph—CH₂CH₂CH₃
CH₃—Ph—COO—Ch—CF=CF—C≡C—Ph—CH₂CH₂CH₃
CH₂O—Ph—COO—Ph—CF=CF—C≡C—Ph—CH₃CH₂CH₂

EXAMPLE 16

Into a 200 ml three-necked flask, 1.34 g of Pd(PPh₃)₂Cl₂, 0.37 g of CuI and 100 ml of triethylamine were charged under an argon atmosphere, and 4.7 g (0.04 mol) of 4-ethynyl toluene was dropwise added at room temperature. After stirring the mixture for 15 minutes, 8.4 g (0.04 mol) of iodotrifluoroethylene was further dropwise added thereto, and the mixture was reacted at room temperature for 20 hours.

After filtration, triethylamine was distilled off, and 100 ml of methylene chloride was added to the residue. The mixture was washed with a 5% hydrochloric acid aqueous solution and then with water, and dried. Then, the solvent was distilled off. The obtained crude oil was purified by silica gel column chromatography to obtain 4.0 g (yield: 51%) of 1-p-toluyl-3,4,4-trifluoro-3-buten-1-yne.

CH₃—Ph—C≡C—CF=CF₂

Then, into a 100 ml three-necked flask, 5.0 g (0.021 mol) of 3-fluoro-4-iodotoluene and 50 ml of dry ether were charged under an argon atmosphere, and cooled to −78° C. Then, 13.7 ml (0.022 mol) of a n-hexane solution of n-butyl lithium (1.61M) was dropwise added thereto over a period of 15 minutes. Then, the mixture was further stirred for 30 minutes, and then the THF solution of 2.77 g (0.014 mol) of the previously obtained 1-p-toluyl-3,4,4-trifluoro-3-buten-1-yne, was dropwise added thereto at −78° C.

Further, the temperature was raised to room temperature, and the mixture was stirred for one hour. Then, a 1N aqueous solution was added thereto. The organic layer was separated. The aqueous layer was extracted with methylene chloride. The organic layers were put together and dried. Then, the solvent was distilled off, and the obtained crude oil was purified by silica gel column chromatography. The obtained solid was recrystallized from methanol to obtain 1.24 g (yield: 31%) of (E)-3,4-difluoro-1-(p-toluyl)-4-(2-fluoro-4-methylphenyl)-3-buten-1-yne. Here, "Ph(F)" represents a 2-fluoro-1,4-phenylene group.

CH₃—Ph(F)—CF=CF—C≡C—Ph—CH₃

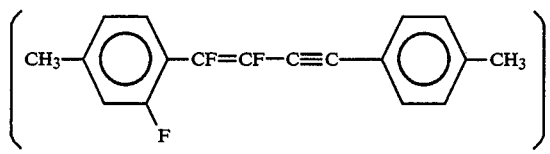

The analytical results of this compound will be shown below.

| ¹⁹F NMR(CDCl₃) δppm from CFCl₃ | −110.9 ppm (m) |
| --- | --- |
|  | −137.0 ppm(d, d, $J_{F-F}$ = 140 Hz) |
|  | −146.6 ppm(d, d, $J_{F-F}$ = 140 Hz) |
| ¹H NMR(CDCl₃) δppm from (CH₃)₄Si | 2.40 ppm(s, 6H) |
|  | 7.20 ppm(m, 7H) |
| MS | m/e 286(M⁺) |
| IR | 2204 cm⁻¹ (C≡C) |
|  | 1160 cm⁻¹ (C—F) |

With respect to (E)-3,4-difluoro-1-(p-toluyl)-4-(2-fluoro-4-methylphenyl)-3-buten-1-yne obtained in Example 16, the maximum absorption wavelength of the absorption band appearing in the ultraviolet absorption region, was measured and found to be 300 nm.

For the measurement of the ultraviolet absorption spectrum, self-recording spectrophotometer UV-3100 (manufactured by Shimadzu Corporation) was employed, and cyclohexane was used as the solvent. The concentration of the sample was 1×10⁻⁵ mol/l, and the measurement was conducted by using a quartz cell having a path length of 1 cm. At that time, the background correction was made with reference to atmospheric air, and the slit width was 2 nm. The measured wavelength region ranged from 500 nm on the long wavelength side to 200 nm on the short wavelength side.

On the other hand, the maximum absorption wavelength of trans-1,2-difluoro-1,2-bis(4-methoxyphenyl)ethylene was 310 nm, and this compound thus had the maximum absorption wavelength on the short wavelength side, as compared with trans-1,2-difluoro-1,2-bis(4-methoxyphenyl)ethylene.

Thus, the ultraviolet wavelength distribution of the sunlight which rises from about 290 nm and the intensity of light of which increases towards the long wavelength overlaps little with the ultraviolet absorption region of the difluoro compound of the present invention, whereby the compound of the present invention has improved stability against ultraviolet rays.

In the same manner as in Example 16, the following compounds can be prepared. Here, "Ph(F)" represents a 2-fluoro-1,4-phenylene group.

CH₃CH₂CH₂—Ph(F)—CF=CF—C≡C—Ph—CH₂CH₂CH₃
CF₃—Ph(F)—CF=CF—C≡C—Ph—CF₃
F—Ph(F)—CF=CF—C≡C—Ph—F
CH₃O—Ph(F)—CF=CF—C≡C—Ph—OCH₃
CH₃CH₂CH₂O—Ph(F)—CF=CF—C≡C—Ph—OCH₂CH₂CH₃
CH₂=CHCH₂—Ph(F)—CF=CF—C≡C—Ph—CH₂CH=CH₂

EXAMPLE 17

To 80 wt % of a liquid crystal composition "ZLI-1565" manufactured by Merck Co., 20 wt % of the compound obtained in Example 16 of the present invention was added to obtain a liquid crystal composition, and its liquid crystal physical property values were measured. The results are shown in Table 1. Further, for the purpose of comparison, the liquid crystal physical property values of ZLI-1565 will also be shown.

TABLE 1

| Liquid crystal physical properties | Liquid crystal composition containing the compound obtained in Example 16 of the present invention | ZLI-1565 |
| --- | --- | --- |
| N-I point (Tc) | 77.3° C. | 86.4° C. |
| Δn | 0.162 | 0.123 |
| Viscosity at 25° C. (cSt) | 14.7 | 15.4 |
| Viscosity at 0° C. (cSt) | 57.5 | 59.2 |

As is evident from Table 1, the liquid crystal composition containing the compound of the present invention is superior to the conventional composition.

EXAMPLE 18

To 80 wt % of a liquid crystal composition "ZLI-1565" manufactured by Merck Co., 20 wt % of the compound obtained in Example 1 of the present invention was added to obtain a liquid crystal composition. As Comparative Examples, a liquid crystal composition composed solely of the liquid crystal composition "ZLI-1565" manufactured by Merck Co. (Comparative Example 1) and a liquid crystal composition prepared by adding 20 wt % of trans-4,4'-bis-(n-propyl)difluorostilbene to 80 wt % of the liquid crystal composition "ZLI-1565" manufactured by Merck Co. (Comparative Example 2) were prepared. These liquid crystal compositions were respectively sealed in liquid crystal cells provided with polarizing plates to obtain STN type liquid crystal display devices.

The display properties of the liquid crystal display devices of this Example and Comparative Example 1 were almost equal, and high speed responses were obtained as compared with the device of Comparative Example 2. Then, the liquid crystal display devices of this Example and Comparative Example 2 were irradiated by an ultraviolet ray carbon arc lamp for 200 hours. After irradiation, the liquid crystal compositions in the respective devices were analyzed.

As a result, in the case of the liquid crystal composition of this Example, no substantial formation of a new compound was observed. On the other hand, in the case of the liquid crystal composition of Comparative Example 2, generation of cis-4,4'-bis-(n-propyl)difluorostilbene was observed.

INDUSTRIAL APPLICABILITY

The compound of the formula (1) of the present invention has a low viscosity and when used as a liquid crystal composition, it improves the response speed even when added in a small amount, whereby low voltage drive, high duty drive and wide temperature range operation will be made possible.

$$R^1-(A^1-Y^1)_m-A^2-CF=CF-C\equiv C-A^3-(Y^2-A^4)_n-R^2 \quad (1)$$

provided that in the formula (1), A¹, A², A³, A⁴, Y¹, Y², m, n, R¹ and R² are as follows:

each of A¹, A², A³ and A⁴, which are independent from one another, is a cyclic group selected from a trans-1,4-cyclohexylene group, a 1,4-cyclohexenylene group and a 1,4-phenylene group, wherein each of such cyclic groups is unsubstituted or substituted by one or more halogen atoms or cyano groups, one or more =CH— groups constituting rings of such cyclic groups may be substituted by nitrogen atoms, and one or more —CH$_2$— groups constituting rings of such cyclic groups may be substituted by oxygen atoms or sulfur atoms;

each of Y$^1$ and Y$^2$ which are independent from each other, is —COO—, —OCO—, —C≡C—, —CH$_2$CH$_2$—, —CH=CH—, —OCH$_2$—, —CH$_2$O— or a single bond;

each of m and n, which are independent from each other, is 0 or 1; and each of R$^1$ and R$^2$ which are independent from each other, is a C$_{1-10}$ alkyl group, a halogen atom or a cyano group, provided that in the case of the alkyl group, an oxygen atom, a carbonyloxy group or an oxycarbonyl group may be interposed in a carbon-carbon bond of the alkyl group or in a carbon-carbon bond between this alkyl group and the adjacent cyclic group, some of carbon-carbon bonds in the alkyl group may be triple bonds or double bonds, one —CH$_2$— group in the alkyl group may be substituted by a carbonyl group, and some or all of hydrogen atoms in the alkyl group may be substituted by fluorine atoms.

Further, its durability against e.g. ultraviolet rays is higher than a difluorostilbene type liquid crystal, and its characteristic of low viscosity can be sufficiently utilized.

We claim:

1. A difluoro-derivative compound of the following formula (1):

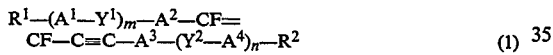  (1)

provided that in the formula (1), A$^1$, A$^2$, A$^3$, A$^4$, Y$^1$, Y$^2$, m, n, R$^1$ and R$^2$ are as follows:

each of A$^1$, A$^2$, A$^3$ and A$^4$, which are independent from one another, is a cyclic group selected from the group consisting of a trans-1, 4 -cyclohexylene group, a 1,4 -cyclohexenylene group and a 1,4-phenylene group, at least one of A$^2$ and A$^3$ being a trans-1,4-cyclohexylene group, wherein each of such cyclic groups is unsubstituted or substituted by one or more halogen atoms or one or halogen atoms or cyano groups, one or more =CH— groups constituting rings of such cyclic groups can be substituted by nitrogen atoms, and one or more —CH2— groups constituting rings of such cyclic groups can be substituted by oxygen atoms or sulfur atoms;

each of Y$^1$ and Y$^2$, which are independent from each other, is —COO—, —OCO—, —C≡C—, —CH$_2$CH$_2$—, —CH=CH—, —OCH$_2$—, —CH$_2$O— or a single bond;

each of m and n, which are independent from each other, is 0 or 1; and each of R$^1$ and R$^2$, which are independent from each other, is a C$_{1-10}$ alkyl group, a halogen atom or a cyano group, provided that in the case of the alkyl group, an oxygen atom, a carbonyloxy group or an oxycarbony group can be interposed in a carbon-carbon bond of the alkyl group or in a carbon-carbon bond between this alkyl group and the adjacent cyclic group, some of carbon-carbon bonds in the alkyl group can be triple bonds or double bonds, one —CH2— group in the alkyl group can be substituted by a carbonyl group, and some or all of hydrogen atoms in the alkyl group can be substituted by fluorine atoms.

2. The difluoro-derivative compound according to claim 1, which has the following formula (2):

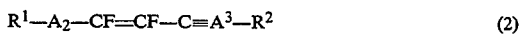  (2)

provided that in the formula (2), A$^2$, A$^3$, R$^1$ and R$^2$ are as defined with respect to the formula (1).

3. A compound having a liquid crystal property selected from difluoro-derivative compounds of the following formula (1):

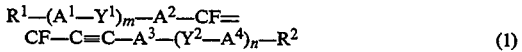  (1)

provided that in the formula (1), A$^1$, A$^2$, A$^3$, A$^4$, Y$^1$, Y$^2$, m, n, R$^1$ and R$^2$ are as follows:

each of A$^1$, A$^2$, A$^3$ and A$^4$, which are independent from one another, is a cyclic group selected from the group consisting of a trans-1,4-cyclohexylene group, a 1,4-cyclohexenylene group and a 1,4-phenylene group, at least one of A$^2$ and A$^3$ being a trans-1,4-cyclohexylene group, wherein each of such cyclic groups is unsubstituted or substituted by one or more halogen atoms or one or halogen atoms or cyano groups, one or more =CH— groups constituting rings of such cyclic groups can be substituted by nitrogen atoms, and one or more —CH$_2$— groups constituting rings of such cyclic groups can be substituted by oxygen atoms or sulfur atoms;

each of Y$^1$ and Y$^2$, which are independent from each other, is —COO—, —OCO—, —C≡C—, —CH$_2$CH$_2$—, —CH=CH—, —OCH$_2$—, —CH$_2$O— or a single bond;

each of m and n, which are independent from each other, is 0 or 1; and each of R$^1$ and R$^2$, which are independent from each other, is a C$_{1-10}$ alkyl group, a halogen atom or a cyano group, provided that in the case of the alkyl group, an oxygen atom, a carbonyloxy group or an oxycarbony group can be interposed in a carbon-carbon bond of the alkyl group or in a carbon-carbon bond between this alkyl group and the adjacent cyclic group, some of carbon-carbon bonds in the alkyl group can be triple bonds or double bonds, one —CH2— group in the alkyl group can be substituted by a carbonyl group, and some or all of hydrogen atoms in the alkyl group can be substituted by fluorine atoms.

4. The compound according to claim 3, which is selected from difluoro-derivative compounds of the following formula (2):

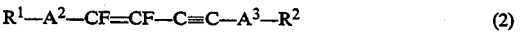  (2)

provided that in the formula (2), R$^2$, A$^3$, R$^1$ and R$^2$ are as defined with respect to the formula (1).

5. A liquid crystal composition containing at least one difluoro-derivative compound of the following formula (1):

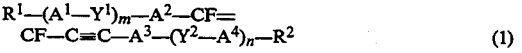  (1)

provided that in the formula (1), A$^1$, A$^2$, A$^3$, A$^4$, Y$^1$, Y$^2$, m, n, R$^1$ and R$^2$ are as follows:

each of $A^1$, $A^2$, $A^3$ and $A^4$, which are independent from one another, is a cyclic group selected from the group consisting of a trans-1,4-cyclohexylene group, a 1,4-cyclohexenylene group and a 1,4-phenylene group, at least one of $A^2$ and $A^3$ being a trans-1,4-cyclohexylene group, wherein each of such cyclic groups is unsubstituted or substituted by one or more halogen atoms or one or halogen atoms or cyano groups, one or more =CH— groups constituting rings of such cyclic groups can be substituted by nitrogen atoms, and one or more —CH$_2$— groups constituting rings of such cyclic groups can be substituted by oxygen atoms or sulfur atoms;

each of $Y^1$ and $Y^2$, which are independent from each other, is —COO—, —OCO—, —C≡C—, —CH$_2$CH$_2$—, —CH=CH—, —OCH$_2$—, —CH$_2$O— or a single bond;

each of m and n, which are independent from each other, is 0 or 1; and each of $R^1$ and $R^2$, which are independent from each other, is a C$_{1-10}$ alkyl group, a halogen atom or a cyano group, provided that in the case of the alkyl group, an oxygen atom, a carbonyloxy group or an oxycarbony group can be interposed in a carbon-carbon bond of the alkyl group or in a carbon-carbon bond between this alkyl group and the adjacent cyclic group, some of carbon-carbon bonds in the alkyl group can be triple bonds or double bonds, one —CH$_2$— group in the alkyl group can be substituted by a carbonyl group, and some or all of hydrogen atoms in the alkyl group can be substituted by fluorine atoms.

6. The liquid crystal composition according to claim 5, which contains at least one difluoro-derivative compound of the following formula (2):

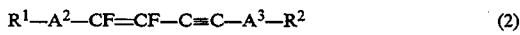

provided that in the formula (2), $A^2$, $A^3$, $R^1$ and $R^2$ are as defined with respect to the formula (1).

7. A liquid crystal electro-optical device having a liquid crystal composition containing at least one difluoro-derivative compound of the following formula (1):

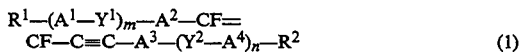

provided that in the formula (1), $A^1$, $A^2$, $A^3$, $A^4$, $Y^1$, $Y^2$, m, n, $R^1$ and $R^2$ are as follows:

each of $A^1$, $A^2$, $A^3$, and $A^4$, which are independent from one another, is a cyclic group selected from the group consisting of a trans-1,4-cyclohexylene group, a 1,4-cyclohexenylene group and a 1,4-phenylene group, at least one of $A^2$ and $A^3$ being a trans-1,4-cyclohexylene group, wherein each of such cyclic groups is unsubstituted or substituted by one or more halogen atoms or one or halogen atoms or cyano groups, one or more =CH— groups constituting rings of such cyclic groups can be substituted by nitrogen atoms, and one or more —CH$_2$— groups constituting rings of such cyclic groups can be substituted by oxygen atoms or sulfur atoms;

each of $Y^1$ and $Y^2$, which are independent from each other, is —COO—, —OCO—, —C≡C—, —CH$_2$CH$_2$—, —CH=CH—, —OCH$_2$—, CH$_2$O— or a single bond;

each of m and n, which are independent from each other, is 0 or 1; and each of $R^1$ and $R^2$, which are independent from each other, is a C$_{1-10}$ alkyl group, a halogen atom or a cyano group, provided that in the case of the alkyl group, an oxygen atom, a carbonyloxy group or an oxycarbony group can be interposed in a carbon-carbon bond of the alkyl group or in a carbon-carbon bond between this alkyl group and the adjacent cyclic group, some of carbon-carbon bonds in the alkyl group can be triple bonds or double bonds, one —CH$_2$— group in the alkyl group can be substituted by a carbonyl group, and some or all of hydrogen atoms in the alkyl group can be substituted by fluorine atoms.

8. The liquid crystal electro-optical device according to claim 7, which has a liquid crystal composition containing at least one difluoro-derivative compound of the following formula (2) interposed between substrates provided with electrodes:

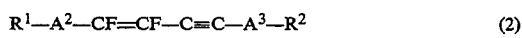

provided that in the formula (2), $A^2$, $A^3$, $R^1$ and $R^2$ are as defined with respect to the formula (1).

9. The difluoro-derivative compound according to claim 2, wherein $A^2$ is a trans-1,4-cyclohexylene group.

10. The difluoro-derivate compound according to claim 2, wherein $A^3$ is a trans-1,4-cyclohexylene group.

11. The difluoro-derivative compound according to claim 2, wherein $A^2$ and $A^3$ are trans-1,4-cyclohexylene groups.

12. The compound having a liquid crystal property according to claim 4, which is selected from difluoro-derivative compounds, wherein $A^2$ is a trans-1,4-cyclohexylene group.

13. The compound having a liquid crystal property according to claim 4, which is selected from difluoro-derivative compounds, wherein $A^3$ is a trans-1,4-cyclohexylene group.

14. The compound having a liquid crystal property according to claim 4, which is selected from difluoro-derivative compounds, wherein $A^2$ and $A^3$ are trans-1,4-cyclohexylene groups.

15. The liquid crystal composition according to claim 6, which contains at least one difluoro-derivative compound, wherein $A^2$ is a trans-1,4-cyclohexylene group.

16. The liquid crystal composition according to claim 6, which contains at least one difluoro-derivative compound, wherein $A^3$ is trans-1,4-cyclohexylene group.

17. The liquid crystal composition according to claim 6, which contains at least one difluoro-derivative compound, wherein $A^2$ and $A^3$ are trans-1,4-cyclohexylene groups.

18. The liquid crystal electro-optical device according to claim 8, which has a liquid crystal composition containing at least one difluoro-derivative compound wherein $A^2$ is a trans-1,4-cyclohexylene group, interposed between substrates provided with electrodes.

19. The liquid crystal electro-optical device according to claim 8, which has a liquid crystal composition containing at least one difluoro-derivative compound wherein $A^3$ is a trans-1,4-cyclohexylene group, interposed between substrates provided with electrodes.

20. The liquid crystal electro-optical device according to claim 8, which has a liquid crystal composition containing at least one difluoro-derivative compound wherein $A^2$ and $A^3$ are trans-1,4-cyclohexylene groups, interposed between substrates provided with electrodes.

* * * * *